Figure 1B:
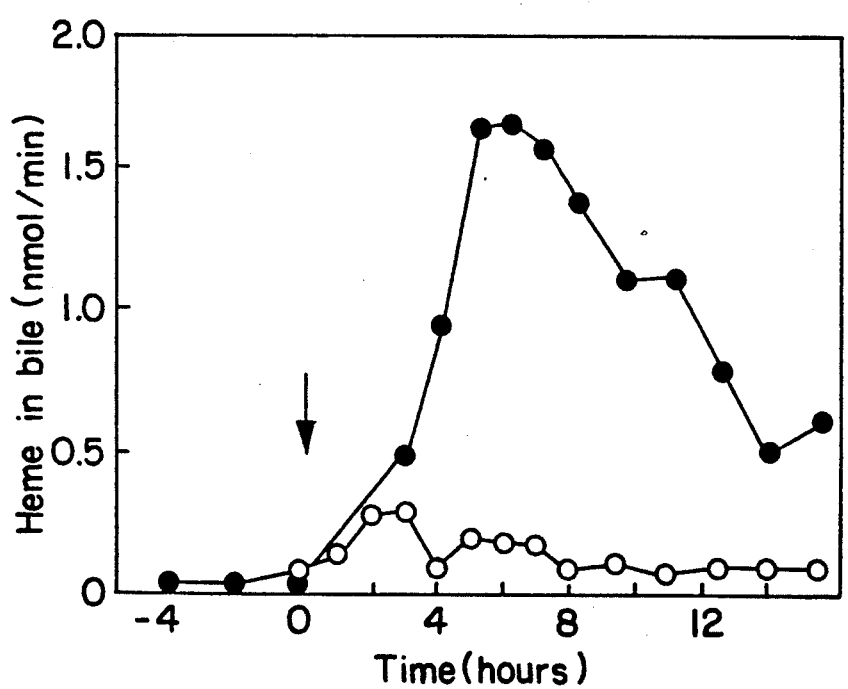
Figure 1C:
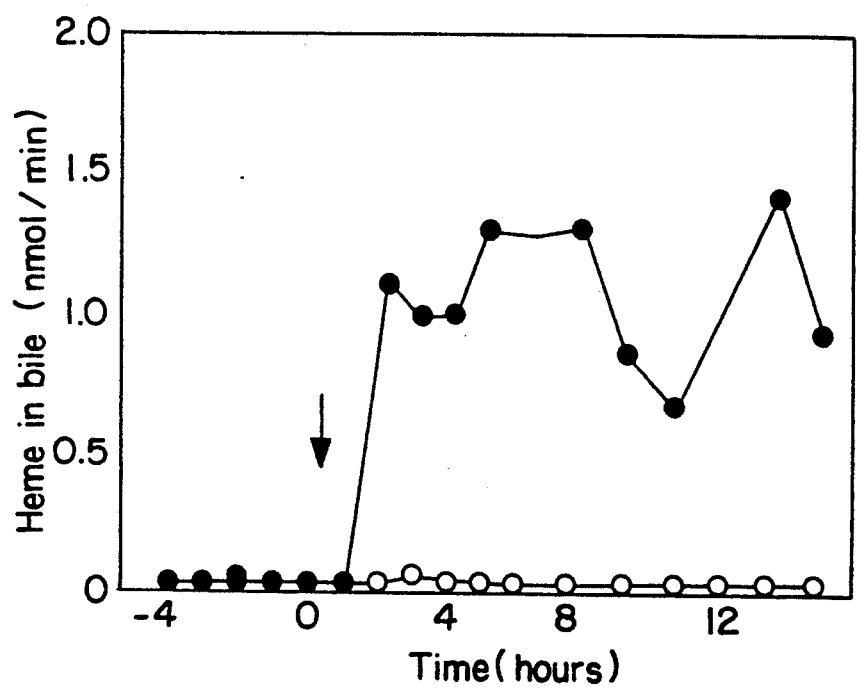
Figure 1E:
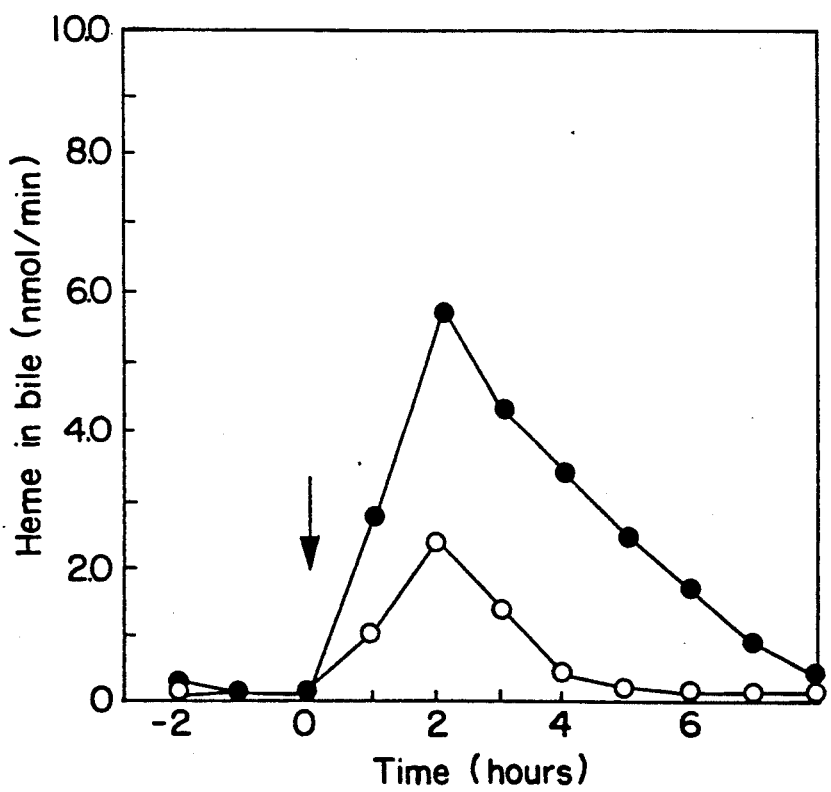
Figure 2A:
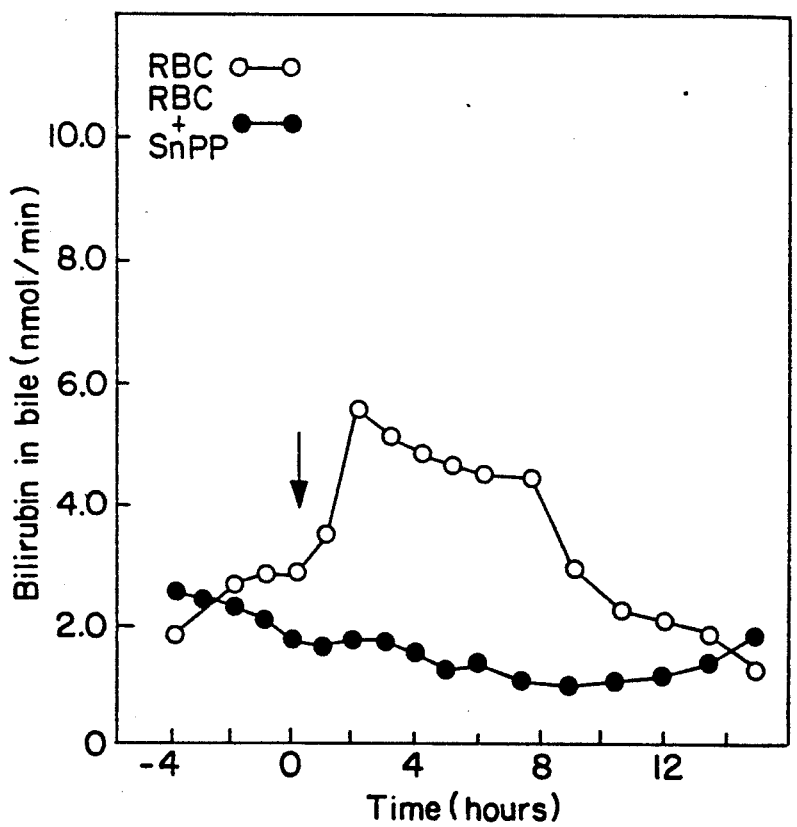
Figure 2B:
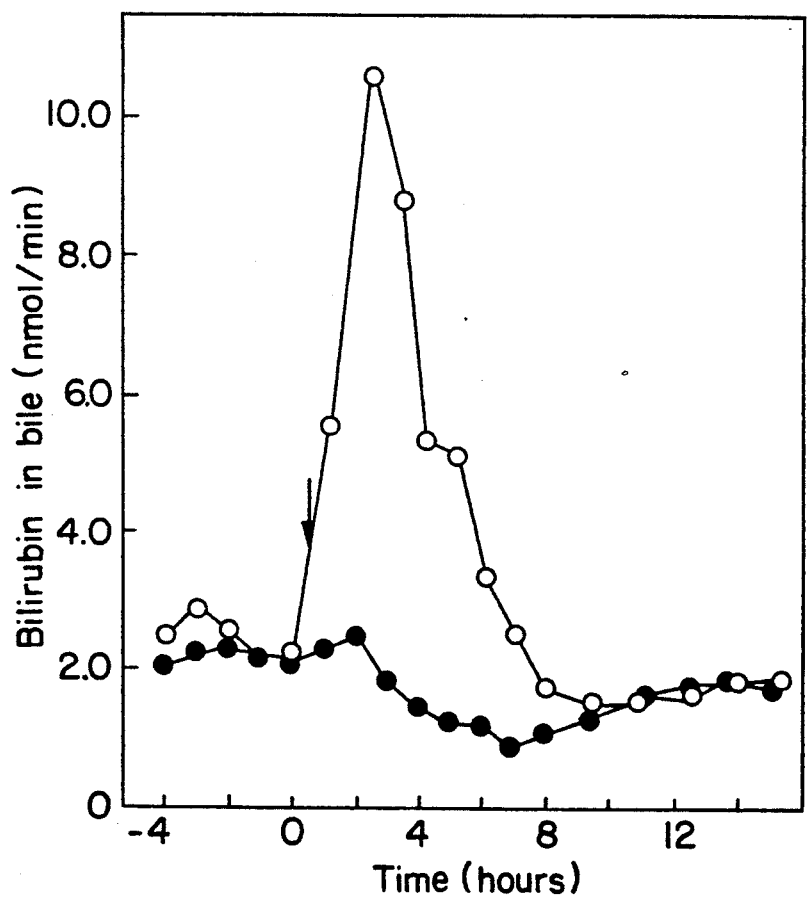
Figure 2C:
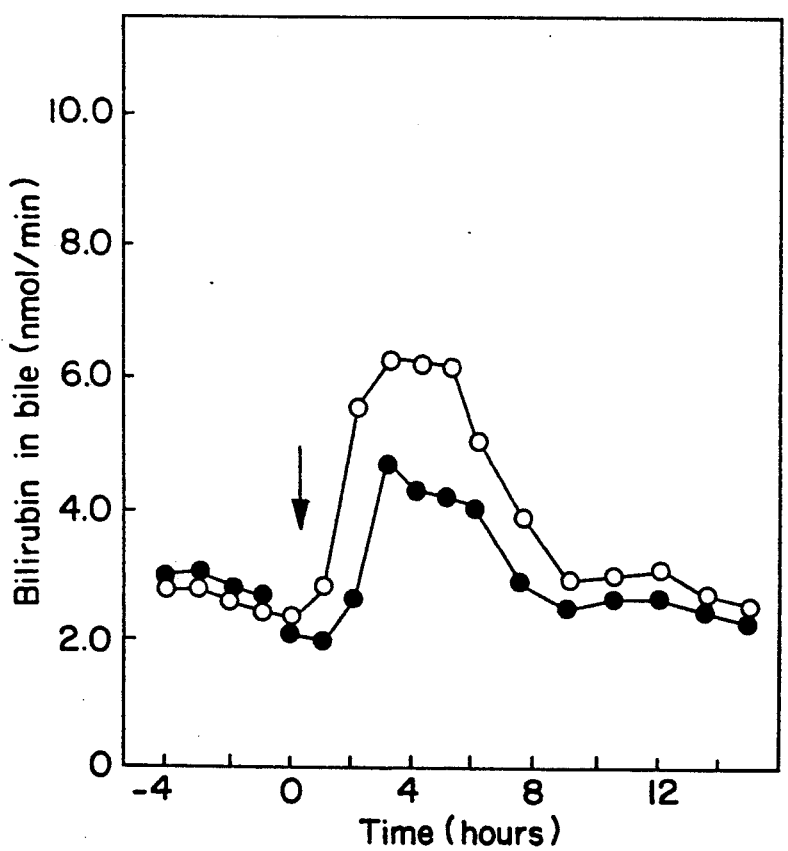
Figure 2D:
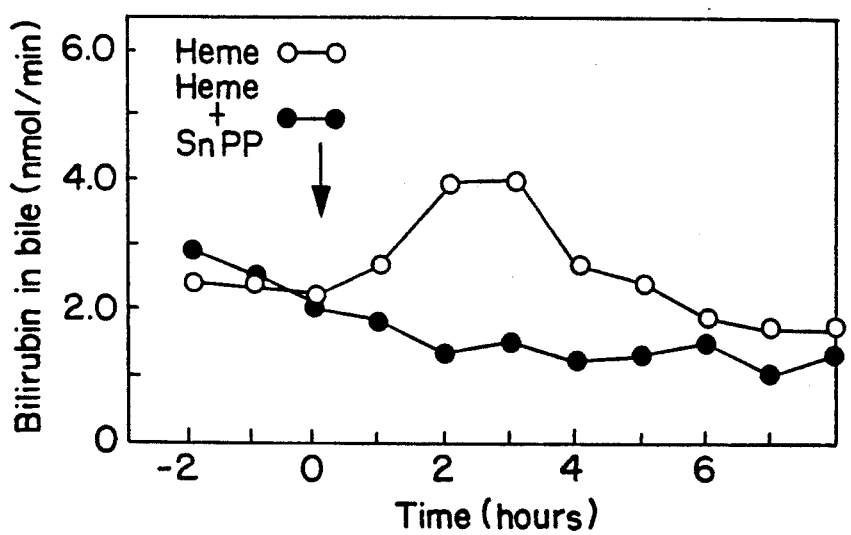
Figure 2E:
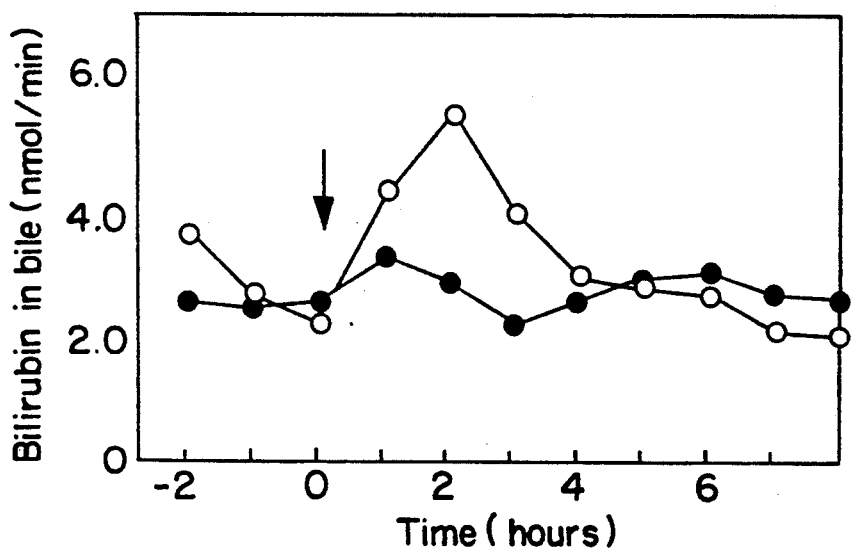
Figure 2F:
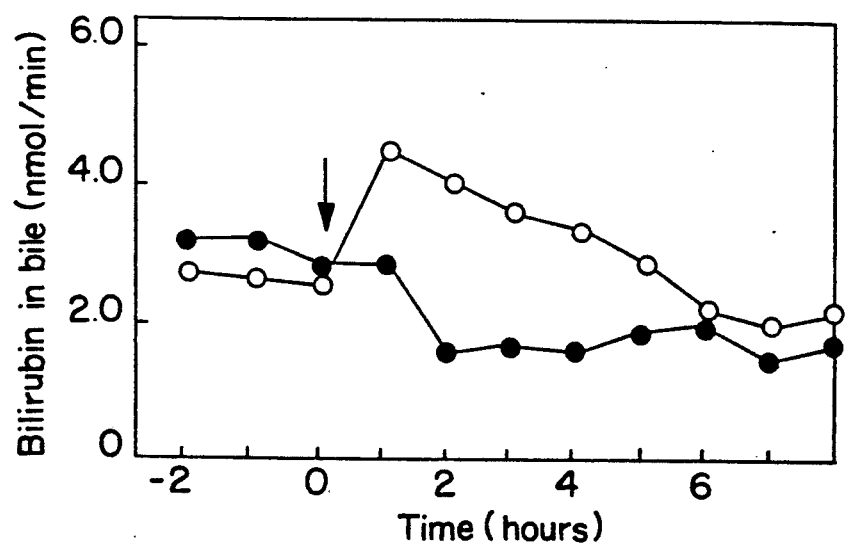

United States Patent [19]

Kappas et al.

[11] Patent Number: 5,162,313
[45] Date of Patent: Nov. 10, 1992

[54] CONTROL OF HEME AND IRON CONCENTRATIONS IN BODY TISSUES

[75] Inventors: Attallah Kappas; George S. Drummond, both of New York, N.Y.

[73] Assignee: The Rockefeller University, New York, N.Y.

[21] Appl. No.: 485,170

[22] Filed: Feb. 26, 1990

Related U.S. Application Data

[63] Continuation-in-part of Ser. No. 325,086, Mar. 16, 1989, abandoned.

[51] Int. Cl.$^5$ .................. A61K 31/33; A61K 31/555
[52] U.S. Cl. .................................. 514/183; 514/185
[58] Field of Search ............................ 514/183, 185

Primary Examiner—Stanley J. Friedman
Attorney, Agent, or Firm—Wyatt, Gerber, Burke and Badie

[57] ABSTRACT

The administration of tin protoporphyrin, tin mesoporphyrin or tin diiododeuteroporphyrin to mammals, notably humans, increases the rate at which heme is excreted by mammals, and is useful for treatment of body tissue injury associated with hemorrhage in the body.

5 Claims, 14 Drawing Sheets

FIG. IA
Increased heme output in bile after Sn-PP administration
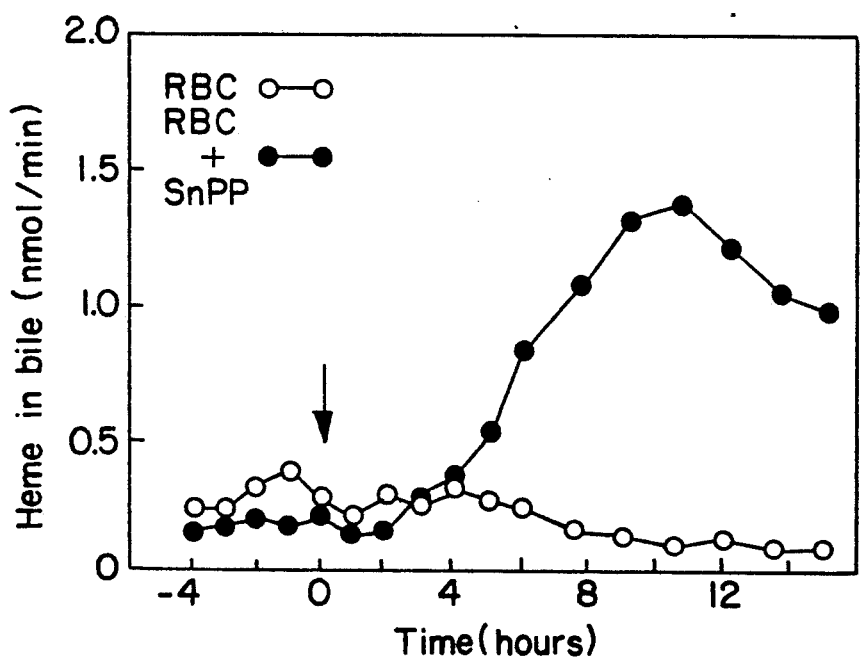

Increased heme output in bile after Sn-PP administration

Increase heme output in bile after Sn-PP administration

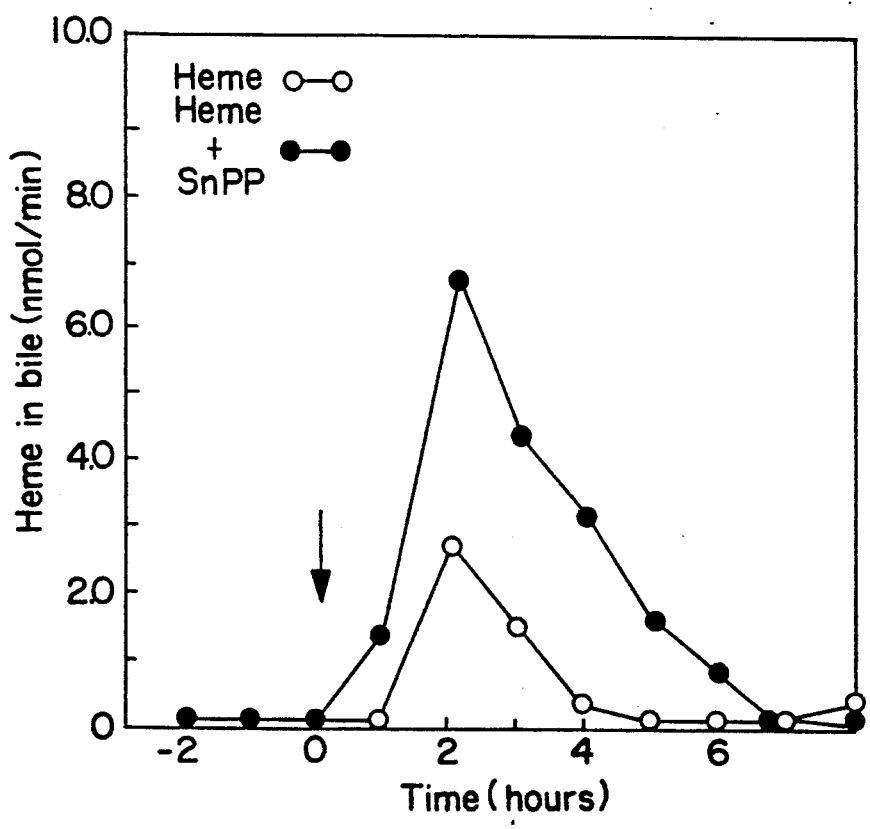
FIG. ID
Increased heme output in bile after Sn-PP administration

Increased heme output in bile after Sn-PP administration

FIG. IF
Increased heme output in bile after Sn-PP administration
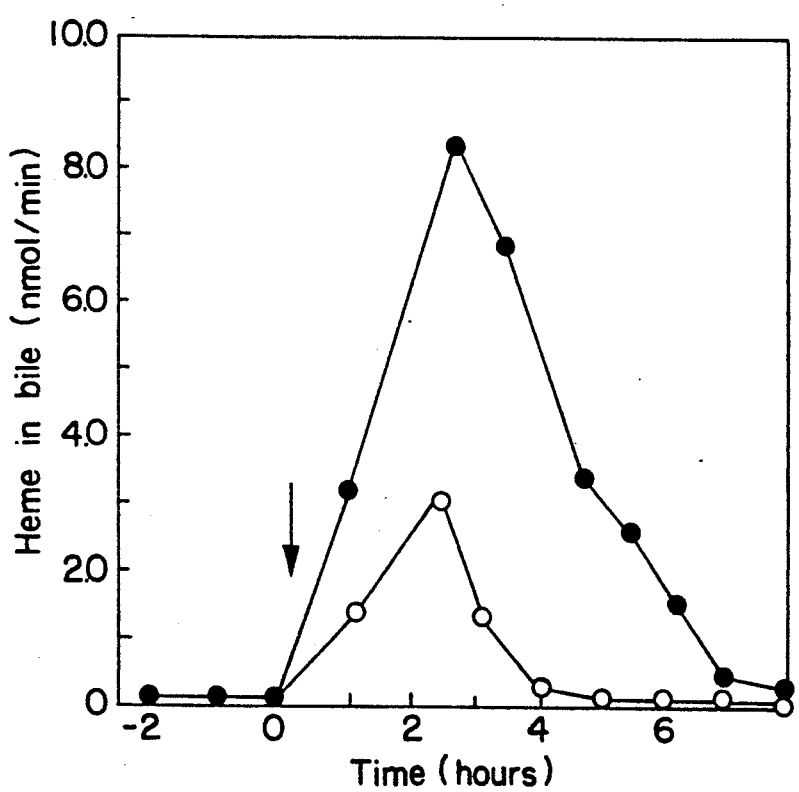

Decreased bilirubin output in bile after Sn-PP administration

Decreased bilirubin output in bile after Sn-PP administration

Decreased bilirubin output in bile after Sn-PP administration

Decreased bilirubin output in bile after Sn-PP administration

Decreased bilirubin output in bile after Sn-PP administration

Decreased bilirubin output in bile after Sn-PP administration

HPLC analyses of bilirubin and heme in bile in Sn-PP markedly increases heme excretion while decreasing bilirubin excretion in bile (bottom panels).

IRON EXCRETION IN BILE AFTER Sn-PP ADMINISTRATION

CONTROL OF HEME AND IRON CONCENTRATIONS IN BODY TISSUES

RELATED APPLICATION

This application is a continuation-in-part of application Ser. No. 07/325,086 filed Mar. 16, 1989, now abandoned.

The synthetic heme analog tin protoporphyrin-IX (Sn-PP) is a potent inhibitor of heme oxygenase, the rate limiting enzyme in the degradation of heme to bile pigments, in addition Sn-PP is also known for its utility as a suppresant of hyperbilirubinemia in neonatal mammals and for its ability to reduce plasma bilirubin levels in a variety of forms of naturally occurring or experimentally induced jaundice in animals and man.

It has now been discovered that this potent pharmacological agent is also useful for enhancing the rapid excretion of both heme itself and of iron in mammals. When heme oxygenase is inhibited by Sn-PP administration in vivo, the liver responds by rapidly excreting large amounts of heme via the biliary system into the gut; each molecule of heme so excreted, carries with it an atom of iron which is also excreted.

Iron protoporphyrin-IX, also called heme, or more accurately ferroprotoporphyrin IX, is the specific natural porphyrin isomer found in mammalian blood. It is an essential component of the respiratory chain and in energy transfer reactions which take place in the mammalian body. It is synthesized and degraded by known metabolic routes involving known enzymatic reactions.

The formation and metabolism of heme in the mammalian body is well known and understood. Heme itself consists of an iron part and an organic part. The latter consists of four pyrrole rings linked by methene bridges to form a tetrapyrrole ring. In protoporphyrin-IX there are four methyl, two vinyl, and two propionate side chains attached to the tetrapyrrole ring. The iron atom in heme binds to the four nitrogens in the center of this tetrapyrrole ring.

The synthesis and catabolism of heme involves a number of enzymes, intermediate structures and appropriate feed-back mechanisms. In the catabolic steps of heme metabolism, heme first undergoes a ring opening (oxidative) reaction to form the linear tetrapyrrole biliverdin, which is in turn reduced to form the yellow pigment bilirubin. The latter, in high concentrations is neurotoxic to newborn animals, including man; and it exerts cellular toxicities in high concentrations in adult tissues as well. Bilirubin is transported by various plasma proteins (e.g., albumin,) to the liver for ultimate disposal. Bilirubin is also formed in the liver as well. Bilirubin in the liver is converted to the corresponding diglucoronide which is water soluble permitting its excretion into bile. The iron atom derived from heme catabolism is, in normal circumstances, recycled for further use. Because of the essential role of this metallin body metabolism, it is avidly preserved and except for frank bleeding (e.g., menstrual blood loss, hemorrhage from other causes) no systematic mechanism exists for disposing of excess iron released into tissues through abnormal mechanisms.

There are a number of pathological conditions associated with the metabolism of heme in mammals. One of the most common and potentially severe is excess hyperbilirubinemia—the so-called "jaundice of the newborn." This circumstance arises from undesirably high rates of bilirubin formation and the retention in the circulation of this pigment in the blood of newborn mammals. This condition is prevented or greatly ameliorated by the parenteral administration of Sn-PP which retards the rate of heme degradation.

There are conditions where there are high concentrations of heme in the body and where it would be therapeutically beneficial to establish a means for enhancing the excretion of such excess heme as promptly and in as sustained a manner as possible. "Jaundice of the newborn" itself is one such condition since the excess plasma bilirubin tends in this disorder to derive from the great excess of heme in the body which results from the rapid lysis of fetal erythrocytes immediately after birth and their gradual replacement by erythrocytes more suitable to oxygen transport in extra-uterine life. Thus in treating severe "jaundice of the newborn" it is desirable not only to block heme catabolism to bilirubin but, to additionally enhance the excretion of the untransformed heme molecule itself.

Acute and chronic hemolysis in adults and children, (e.g. thallasemia, sickle cell disease), which may result from genetic defects in erythrocytes or from exposure to chemical toxins of a wide variety of types, (e.g. metals), can lead to release into the bloodstream and body tissues of excess amounts of heme. Patients who require heme administration directly to suppress clinical activity of genetic diseases such as the porphyrias; patients who require repeated transfusions for therapy of severe anemias (e.g., aplastic); patients who have had internal bleeding from a variety of causes (e.g., clotting defects, naturally occurring or resulting from the anti-coagulent treatment; surgery; trauma) all will have periods when there are excess heme concentrations in tissues. The feed-back physiological mechanisms in which normal amounts of heme participate are exquisitely sensitive and their perturbation by excess amounts of heme can greatly alter processes ranging from the control of endogenous heme synthesis and degradation itself, to processes affecting heme functions, as when heme serves as a prosthetic group for an important enzyme (e.g., tryptophan pyrrolase, catalase), to processes where heme regulates such vital heme-proteins as cytochrome P-450, the oxygenase which plays a crucial role in the detoxification of drugs, carcinogens and a host of enviromental pollutants.

Thus maintenance of a proper equilibrium or balance of tissue heme content is essential to the normal physiological functioning of cells. When this equilibrium is disturbed by any condition characterized by excess heme—as exemplified by the circumstances listed above—it would be clinically valuable to have a pharmacological mechanism for restoring the equilibrium state of heme in cells by facilitating the excretion of the excess amount of heme from the body.

Sn-PP has been discovered to manifest this utility as a pharmacological agent.

In association with but independent of the conditions described above, excess iron also accumulates in the body and this accumulation of the metal over time, can produce deleterious and even lethal consequences for the host. This excess of iron may derive from several sources; e.g. cooking methods (iron pots) or directly via the diet (e.g., iron-overload induced cutaneous porphyria) from excess therapeutic administration of the metal in an attempt to vigorously treat unresponsive anemias; from hypertransfusions to which certain patients with blood disorders are subject; idiopathically from the disorders collectively known as "hemachromatosis"; from certain industrial exposures; but the most common causes of excess iron deposition in tissues, and the resultant pathologic consequences which derive thereof, are a consequence of common congenital hemolytic anemias such as sickle cell disease, the various forms of thallasemia, G-6-PD deficiency, hereditary spherocytosis and the like. In these disorders, a greatly shortened red cell life span results in continuous large depositions of iron in tissues to an extent exceeding the capacity of the body to re-utilize the metal. Thus tissue concentrations of iron rise to very high, toxic levels and lead to impairment of vital organ functions manifest and for example by cardiomyopathy, pancreatic insufficienty (diabetes) and generalized endocrine failure.

There is no physiological mechanism for excreting this excess of iron and the only generally available therapeutic modality for this purpose is a pharmacological agent known as desferrioxamine. This agent is not specific for iron however and chelates other metals as well; it must in order to be reasonably effective be given intramuscularly and causes substantial local inflammation at the site of injection. Further, original suggestions that it was non-toxic have proved incorrect and a large number of toxic reactions (including death) in treated patients have now been reported to occur after its use.

Sn-PP displays the extremely advantageous property of greatly enhancing the biliary excretion of iron into the intestinal contents where the metal is eliminated. Sn-PP acts in this additional fashion by blocking the binding of heme to heme oxygenase, thus preventing the release of iron which normally occurs in the process of heme catabolism and allowing one atom or iron to be excreted into the intestine with every molecule of uncatabolized heme.

Sn-PP is therefore especially useful in those millions of individuals afflicted with such chronic abnormalities of heme and iron metabolism as for example, those with sickle cell disease, which is so prominent in the United States and Africa; those with thallasemia who inhabit the Mediterranean basin and the descendents of this population group in the United States, and those with primary and secondary forms of hemochromatosis. Sn-PP is also useful in veterinary practice in selected circumstances— as for example when hemochromatosis occurs in especially valuable breeding animals as a secondary consequence of equine infectious anemia—or when animals suffer hemolysis from some of the same causes as do humans (i.e., poisonings from certain environmental chemicals).

In addition to enhancing the rate at which heme is excreted from the bile, Sn-PP is also useful in a tissue injury associated with hemorrhage in other parts of the body. Thus, Sn-PP is also useful for treating cerebral hemorrhage, trauma, hemorrhage into joint spaces or bleeding into body cavity. Whenever a body tissue is injured, hemoglobin usually accumulates at the site of the injury and, inevitably, there is a breakdown of heme by heme oxygen and associated enzymes, with a consequent release of free iron. The free iron which is thus released would then mediate lipid peroxidation of cell membranes thereby severely destroying or damaging such cells.

The following experiments demonstrate the ability of Sn-PP in increasing the rate at which heme, and also iron, is excreted from the liver into the intestinal tract by the administration of Sn-PP. These experiments are not to be considered as limited to Sn-PP. Substantially similar efficacious results may be obtained by administering Sn-Mesoporphyrin (Sn-MP), and Sn-Diiododeuteroporphyrin (Sn-DIDP), or mixtures thereof together and/or with Sn-PP and other metalloporphyrins, such as Zn-protoporphyrin, Zn-mesoporphyrin and Zn-deuteroporphyrin 2,4-bis glycol.

The results of these studies are shown in FIGS. 1A-F, 2A-F, 3 and 4.

FIG. 1 shows that the amount of heme excreted into bile by rats, who have been administered heme or damaged red cells (as an alternative source of excess heme) and then treated with Sn-PP in parallel experiments, increases markedly in animals treated with the synthetic metalloporphyrin as compared with the amounts of heme in bile of animals not treated with Sn-PP.

FIG. 2 shows that there is a reciprocal decline in the output of bilirubin in bile of the Sn-PP treated animals, consistent with the fact that Sn-PP is blockading heme oxygenase, thus preventing heme degradation to bilirubin and leading to the marked output of heme into bile. It should be noted that this biliary excretion of heme may substantially exceed the reciprocal decline in biliary bilirubin output indicating the great potency of Sn-PP in facilitating heme excretion into the intestinal tract.

Figure 3:
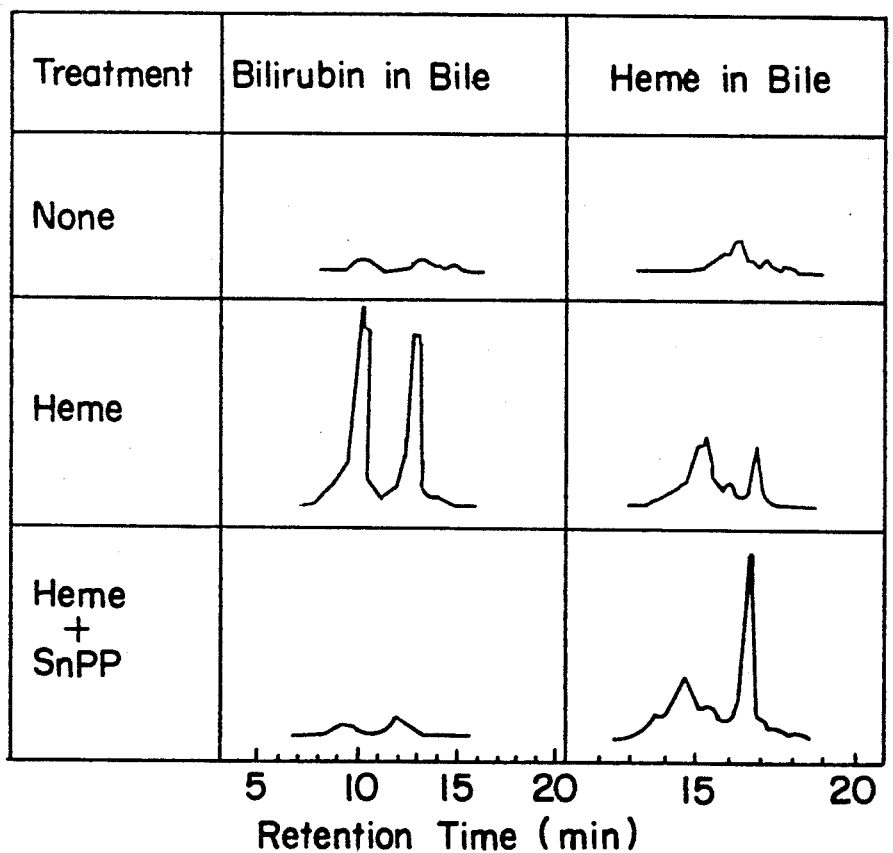

FIG. 3 shows a confirmation of these alterations by HPLC (high performance liquid chromatography) methodology. As noted when heme is administered alone to animals a large output of biliary bilirubin (mono- and di-glucuronide forms) occurs, with a slight output of the excess heme. When Sn-PP is administered with the heme in these animals, it is seen that the bilirubin peaks decline markedly, indicating an inhibited conversion of heme to the bile pigment, while the output of heme, indicated by the large peak in the lower right panel of the figure increases markedly. These findings have been repeatedly confirmed by HPLC, by TLC (thin layer chromatography) and by the quantitation of both heme and bilirubin in bile by appropriate methods.

Figure 4:
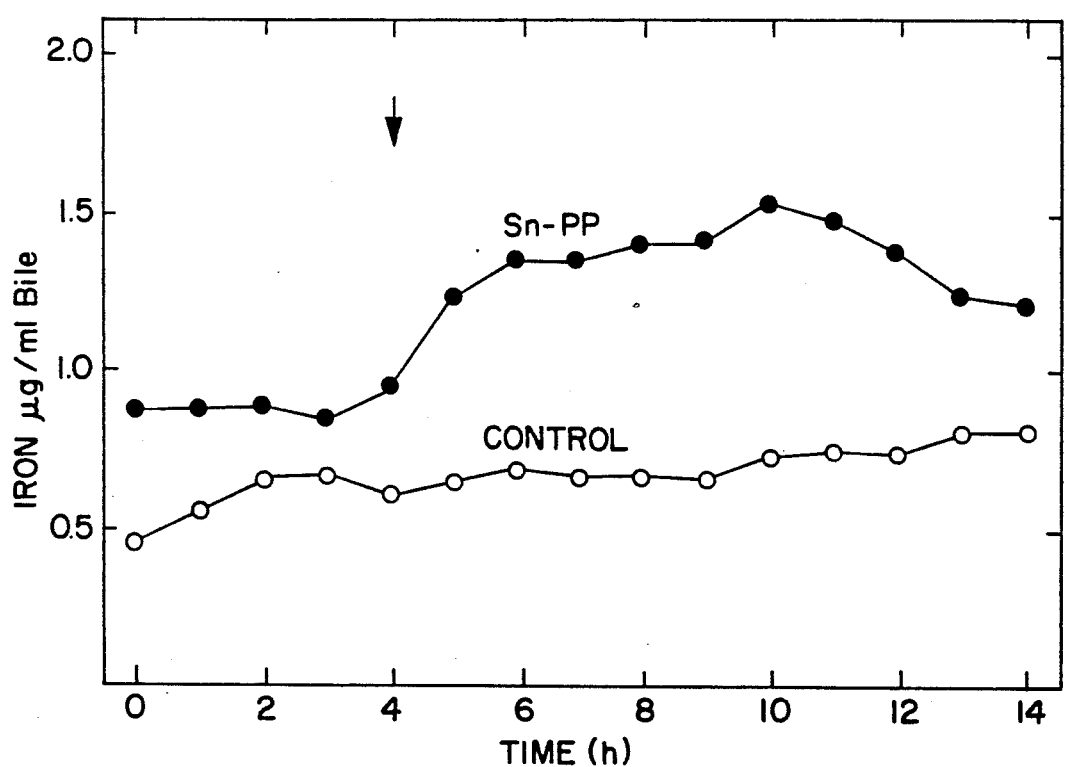

FIG. 4 demonstrates that Sn-PP also greatly enhances the output of iron in bile as determined by graphite furnace atomic absorption analysis. This increased output of iron greatly exceeds the normal biliary concentration of the metal and is consistent with the concurrent increase in output of biliary heme. These findings with biliary iron represent the first demonstration that Sn-PP can substantially enhance the body disposal of this toxic element by taking advantage of a mechanism for its excretion utilizing its natural chelate, heme. This approach to the problem of excess iron disposal is much simpler, less expensive, more physiologic and far more innocuous for the patient than the present therapeutic modality utilized for this purpose.

The details of the procedures by which these determinations were made are as follows:

Male Sprague-Dawley rats (Taconic Farms, Germantown, N.J.) weighing 330-360 g b.w. were used. Sn-PP was dissolved in a small amount of 0.2N NaOH, a 3.5-fold greater volume of 0.9% NaCl was added and the pH was then adjusted to 8.0 by dropwise addition of 0.5N HCl (1). Heme was dissolved in 0.1 ml 0.05N NaOH, and 1.9 ml of rat serum was added dropwise with stirring. Other chemicals utilized were reagent grade and were obtained from Sigma Chemical Co., St. Louis, Mich., or Fisher Scientific, Pittsburgh, Pa.

Bile duct and jugular vein cannulations were carried out in animals anethetized by intraperitoneal injection of sodium pentobarbital. The animals were kept in restraining cages, and before beginning each experiment, including the control period, the animals were allowed to recover from surgery for 3-4 hours so that bile flow and bilirubin output in bile could stabilize. The jugular vein catheter was infused throughout the experiment with a solution containing equal amounts of 0.45% (w/v) NaCl and 5% glucose at a constant rate of 1.1 ml/h using an infusion pump (Harvard Apparatus Co., Millis, Mass.).

Heat-damaged erythrocytes as a source of heme were prepared from rat blood obtained by translumbar puncture of the inferior vena cava. Washed erythrocytes were resuspended to the original volume in 0.9% NaCl, and heated at 49.5° C. for 40-60 minutes as described by Harris et al. [(1956) Clin. Sci. 16,223] and Jandl et al. [(1965) J. Exp. Med. 122,229]. For these experiments the cells were heated for 40 minutes. All experiments were carried out in subdued light. Bile was collected for 60 minute periods in tared plastic tubes, weighted to determine the amount collected and stored in the dark at 4° C.

Bilirubin in bile was determined within 24 hours by the fluorimetric method of Roth [(1967) Clin. Chem. Acta 17,487].

The concentration of heme in bile was determined by the pyridine hemochromogen method by using the reduced-minus-oxidized difference in absorption between 557 nm and 540 mn and an absorption co-efficient of 20.7 $mM^{-1}cm^{-1}$. The pyridine hemochromogen of pure Sn-PP by this method exhibited an absorption peak at 578 nm with troughs at 560 nm and 588 nm, the absorption co-efficient of Sn-PP between 578 nm and 588 nm was 0.89 $mM^{-1}cm^{-1}$, and between 578 nm and 560 nm was 0.60 $mM^{-1}cm^{-1}$. Bile samples used for heme determination could be stored at $-20°$ C. for up to 3 months without loss of heme content. Sn-PP added to bile at a concentration of 140 nmol/ml bile which is greater that those found in these experiments, did not interfere with the determination of heme in bile by the pyridine hemochromogen method. Spectral studies were performed with an Aminco-Chance DW2A spectrophotometer in the split beam mode.

Iron was analyzed in bile samples by graphite furnace atomic absorption analysis, utilizing a stabilized temperature platform and Zeeman background correction. Typically, samples for analysis were prepared by diluting bile 10- or 20-fold in 0.1% Triton X-100. A 10 μl aliquot of the dilution was injected onto the platform and mixed within the furnace with 50 μg of Mg $(NO_3)_2$ in 20% nitric acid (ultrex grade). The temperature program used for iron analysis was as follows:

|  | Step 1 | 2 | 3 | 4 | 5 | 6 |
|---|---|---|---|---|---|---|
| Temp, °C. | 130 | 250 | 1400 | 2400 | 2600 | 20 |
| Ramp, S | 1 | 15 | 10 | 0 | 1 | 1 |
| Hold, S | 45 | 0 | 10 | 7 | 6 | 15 |
| Argon flow, mL/min | 300 | 300 | 300 | 50 | 300 | 300 |
| Read |  |  |  | $-1$ |  |  |

The absorption signal at 248.3 nm was measured in integrated peak area (7 sec) and the data points collected by high speed computer. Iron concentration was then calculated by comparison to a standard curve prepared in dilute control bile (method of additions calibration).

For thin layer chromatography heme and Sn-PP were extracted from bile samples with ethyl ether. After the final extraction step the ethyl ether was evaporated to dryness under a stream of air at room temperature. The dried residues which contained heme and Sn-PP were redissolved in 0.1 ml of a mixture of chloroform and methanol, 1:1 (v/v) and applied to silica gel G plates (Merck, Darmstadt, W. Germany). The plates were developed with benzene, methanol, formic acid (85,15,1.3 [v/v]). Sn-PP (Rf=0.31) could be readily separated from heme (Rf=0.24) in this system and identified by its red fluorescence under long wavelength ultraviolet illumination. Heme did not fluoresce but could be identified visually.

High performance liquid chromatography (HPLC) analysis of bilirubin conjugates and heme in bile was carried out using an HPLC series 3 apparatus (Perkin-Elmer Corp.) and a uBondapak $C_{18}$ column (3.9×300 mm, Waters Assoc.) with a guard column ($C_{18}$ reversed phase 3×300 mm), equipped with a Rheodyne 7105 spetumless injector. Bilirubin glucuronides were extracted from 500 μl samples of bile, which had been previously treated with ammonium sulfate (400 mg) and L-ascorbic acid (20 mg) using a mixture of isopropanol, methanol, dimethyl sulfoxide 6:3:±(v/v), and were then injected into the HPLC apparatus. Bilirubin glucuronides were eluted using a methanol gradient (40-90 percent by volume) in 0.1 M sodium acetate buffer (pH 4.0) containing 5 mM heptanesulfonic acid, at a flow rate of 1 ml/min, and detected by an LC75 spectrophotometer (Perkin-Elmer corp.) set at 436 mn. HPLC analysis of heme in bile was conducted by using the same apparatus and columns but with a methanol gradient (40-90 percent by volume) in 10 mM potassium phosphate buffer (pH 6.0) containing 5 mM tetrabutylammonium hydroxide, using a flow rate of 0.8 ml/min, and detected at a wavelength of 410 mn. Under these conditions heme was completely separated from Sn-PP and the bilirubin derivatives; Sn-PP and the bilirubin conjugates could not be clearly separated.

The effect of Sn-PP on the excretion of heme and bilirubin in bile after the infusion of heat damaged erythrocytes (RBC) or heme in bile duct cannulated rats is demonstrated in FIGS. 1 and 2.

The output of bilirubin and heme in bile was followed for a control period of 5 hours in 16 bile duct cannulated rats, 8 of which (defined as controls) received an intravenous bolus of $8.9 \times 10^9$ heat-damaged erythrocytes/kg b.w., equivalent to 8.5 umol heme/kg b.w., and the other 8 received in addition, Sn-PP (10 umol/kg b.w.) injected intravenously at the same time; similarly 10 bile duct cannulated rats received heme (6.1 umol/kg b.w.) alone or the same dose of heme plus Sn-PP.

In 7 of the 8 control animals receiving heat-damaged erythrocytes alone, no increase in heme output in bile could be detected in the 12-14 h following the erythrocyte infusion alone; in one animal (FIG. 1B) the increase in heme output was negligible. The results of 3 experiments which typify the results in all 8 Sn-PP treated animals are shown in FIG. 1:A,B,C. In the 8 animals which received both the heat-damaged erythrocytes and the Sn-PP infusions, there was, in each instance, a prompt and marked increase in biliary heme excretion (FIG. 1:A,B,C) as measured by the pyridine hemochromogen method. This was confirmed by TLC analysis at periodic intervals throughout the study period. As will be seen, an increase inbiliary bilirubin output developed in each animal infused with heat-damaged erythrocytes (FIG. 2:A,B,C) and this increase was greatly diminished in all but one Sn-PP treated animal.

In these studies with heat-damaged erythrocytes, the combined amounts of heme plus bilirubin in bile, in the two groups of animals (control and Sn-PP treated), were similar, averaging about 50% of the dose of heme administered (as hemoglobin in the heat-damaged erythrocytes alone, of the 50% of heme metabolized, almost the entire amount was recovered as bilirubin; in the Sn-PP treated group in contrast the decline in biliary bilirubin in was accounted for entirely by an increase in heme excretion in bile.

The effect of Sn-PP on the excretion of heme and bilirubin in bile after infusion of exogenous heme in bile duct cannulated rats is also shown in FIGS. 1 and 2.

Bilirubin and heme excretion in bile were monitored in these experiments for a control period of 3 hours in 10 bile duct cannulated rats. Then, 5 of the animals were treated with an intravenous bolus of heme (6.1 umol/kg b.w.) and the other 5 received the same dose of heme plus Sn-PP (10 umol/kg b.w.), also injected intravenously at the same time. The results in 3 studies, which typify those in all studies carried out, are depicted graphically in FIG. 1:D,E,F. In all animals, little or no heme could be detected in bile collected before the heme infusion. Acute infusion of heme alone resulted in the appearance of some heme in bile in all animals studied (FIG. 1:D,E,F). A significant increase in bilirubin output also occurred (FIG. 2:D,E,F) in all animals treated with heme alone.

The effect of Sn-PP treatment, given concurrently with the heme infusion was to elicit in all animals a prompt and marked increase in biliary heme excretion as shown for the 3 typical experiments depicted in FIG. 1:D,E,F. The Sn-PP treatment also diminished the increase in biliary bilirubin resulting from the infusion of heme all in all animals (FIG. 2:D,E,F). The total amount of heme excreted in the bile of the control (i.e., injected with heme along) animals averaged 14% of the dose injected, and an additional 18% was excreted as bilirubin. This degree of conversion of exogenous heme to biliary bilirubin is within the range described by other investigators. Therefore the total amount of exogenous heme recovered in the bile of control animals as both heme and bilirubin averaged 32% of the dose administered. The amounts of heme excreted in bile in the animals treated with Sn-PP and heme, were 3-4-fold greater than the amounts of heme in bile in the control animals treated with heme alone (means of 51% and 14%, respectively of the dose of heme injected). In all cases, the increased output of heme in bile elicited by Sn-PP exceeded the decline in biliary bilirubin content produced by this synthetic metalloporphyrin. HPCL analysis of heme and bilirubin conjugates in bile confirmed these findings (FIG. 3).

The effect of Sn-PP on the output of biliary iron after its administration to bile duct cannulated rats is shown in the representative study in FIG. 4. The output of iron increased markedly—a finding typical of all animals studied. This finding identifies a newly discovered means for excess iron disposal not hitherto known or used therapeutically.

The results of these studies make it clear that the administration of Sn-PP to mammals increases the biliary excretion of excess heme and thus of its contained iron atom as well. They make it clear also that the excess heme which accumulates when the rate of bilirubin production is decreased by the administration of Sn-PP is excreted in the bile and not stored in tissues. More particularly, they make it clear that the administration of Sn-PP to mammals suffering acute or chronic excess of heme or iron will increase the rate at which such heme or iron will be excreted into the intestinal contents.

As previously mentioned, Sn-MP or Sn-DIDP may be used in lieu of Sn-PP either alone or in admixture therewith or together. These therapeutic agents are not only useful for biliary excretion of excess heme in mammals, but are also useful in treating tissue injuries associated with hemorrhage, trauma, cerebral hemorrhage and other body hemorrhages as aforesaid.

The most effective dosage for therapeutic administration will be readily determined by the physician or veterinarian in attendance in accordance with standard well understood procedures. It will normally depend upon the age, weight and general health of the patient as well as the condition being treated. Typical dosages will range from 0.5 to 2.0 umol/kg of body weight in humans. While appreciable variations from this range can be tolerated without unacceptable adverse effects, this range appears to be most practical and has been shown previously to be effective in supressing hyperbilirubinemia in humans.

Any of the usual parenteral rates of administration may be employed. One dosage may be sufficient, or a series of dosage units may be administered at suitable time intervals.

In order to have appropriate dosage units available the therapeutic agent of this invention will normally be prepared in bulk at concentrations of from 2 to 25 grams per liter and subdivided into dosage units containing approximately 2 to 25 milligrams per milliliter of solution. The usual pharmaceutical carriers are isotonic aqueous salt or glucose solutions. However other carriers normally employed or parenteral compositions may be employed including alcohol, alcohol-water and various vegetable oils.

What is claimed is:

1. A method of increasing the rates of which heme and iron are excreted by a mammal in need of such increased disposal because of body tissue injury associated with hemorrhage which comprises parenteral administration to said mammal of a therapeutic agent selected form the group consisting of tin protoporphyrin, tin mesoporphyrin, tin diiododeuteroporphyrin and mixtures thereof in an amount which is sufficient to effect such increase.

2. A method as in claim 1 wherein the mammal is a human.

3. A method as in claim 1 or 2 wherein said therapeutic agent is tin protoporphyrin.

4. A method as in claim 1 or 2 wherein said therapeutic agent is tin mesoporphyrin.

5. A method as in claim 1 or 2 wherein said therapeutic agent is tin diiododeuteroporphyrin.

* * * * *